United States Patent [19]

Henrie, II

[11] Patent Number: 4,728,355
[45] Date of Patent: Mar. 1, 1988

[54] PYRIDAZINYLUREA PLANT REGULATORS

[75] Inventor: Robert N. Henrie, II, East Windsor, N.J.

[73] Assignee: FMC Corporation, Philadelphia, Pa.

[21] Appl. No.: 786,262

[22] Filed: Oct. 10, 1985

[51] Int. Cl.$^4$ .................. A01N 43/58; C07D 237/12; C07D 237/20; C07D 237/22

[52] U.S. Cl. ...................................... 71/92; 544/224; 544/239; 544/240; 544/241

[58] Field of Search ............... 544/224, 239, 240, 241; 71/92, 94

[56] References Cited

U.S. PATENT DOCUMENTS

| | | | |
|---|---|---|---|
| 3,330,641 | 7/1967 | Woods et al. | 71/94 |
| 3,520,886 | 7/1970 | Reicheneder et al. | 544/241 |
| 4,149,872 | 4/1979 | Pilgram | 71/94 |
| 4,193,788 | 3/1980 | Shudo | 71/92 |
| 4,308,054 | 12/1981 | Isogai et al. | 71/94 |
| 4,331,807 | 5/1982 | Okamoto et al. | 71/92 |
| 4,397,678 | 8/1983 | Okamoto et al. | 71/92 |
| 4,411,685 | 10/1983 | Welebir | 71/82 |
| 4,619,686 | 10/1986 | Abdulla et al. | 544/244 |

FOREIGN PATENT DOCUMENTS

| | | | |
|---|---|---|---|
| 0052668 | 6/1982 | European Pat. Off. | 544/224 |
| 0169051 | 1/1986 | European Pat. Off. | 544/224 |

OTHER PUBLICATIONS

Isogai in *Chemical Regulation in Plants*, 17, pp. 27–43 (1982), "Shoot Formation in Response to Cytokinins in Cultured Tobacco Callos and Some Problems Associated with the Phenomenon".

Acta Pharmaceutica Hungarica, 53, 106–114 (1983).
Derwent Abstract #847875 for Japan Patent 58/194804 (11/12/83).
"Plant Growth Regulators and Herbicide Antagonists'"—Recent Advances, edited by J. C. Johnson, Noyes Data Corp. (Publ.) (1982), p. 1.
Bruce and Zwar, *Proc. Roy. Soc. B*, 165, p. 245 (1966).
Kosary et al., *Acta Pharmaceutica Hungarica*, 53, p. 106 (1983).
Ohsawa et al., *Chem. Pharm. Bull.*, 28, p. 3570 (1980).
Zupon et al, *J. Org. Chem.*, vol. 37, No. 19 (1972), pp. 2960–2963.

Primary Examiner—Donald G. Daus
Assistant Examiner—Emily Bernhardt
Attorney, Agent, or Firm—Patrick C. Baker; H. Robinson Ertelt

[57] ABSTRACT

Pyridazinylurea plant regulators of the formula

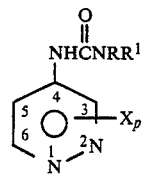

and acid addition salts thereof; wherein R is alkyl or cycloalkyl, R$^1$ is hydrogen or alkyl, each X independently is halogen, alkoxy, alkylthi or alkylsulfonyl, and p is 0, 1 or 2.

8 Claims, No Drawings

PYRIDAZINYLUREA PLANT REGULATORS

BACKGROUND OF THE INVENTION

This invention concerns certain pyridazinylurea compounds and their use as plant regulators.

Plant regulators are hormone-like substances which influence growth and development of plants, as inhibitors or promoters of growth. Sometimes the same compound can both inhibit and promote growth, depending upon the rate of application. Plant regulatory activity is reflected in a variety of ways, including one or more of cell enlargement, leaf and organ abscission, retardation of senescence, release of apical dominance, fruit set and growth, leaf growth, light response, protein synthesis, and other effects. In economic crops and ornamentals, plant regulators have enormous potential as herbicides, rooting promoters, flowering stimulants, fruit developers, and as agents to control or induce seedlessness, plant shape, and the setting, thinning and dropping of fruit. The most familiar classes of plant regulators are the auxins, gibberellins, cytokinins, abscisic acid and ethylene, but the search continues for even more active plant regulating compounds, including compounds having specific forms of regulator activity.

Representative of research efforts in the field are the compounds disclosed in U.S. Pat. Nos. 4,063,928 (substituted pyridinyloxy(thio)phenyl acetamides, ureas and urea derivatives), 4,193,788 (N-(2-chloro-4-pyridyl-)ureas and thioureas), 4,308,054 (other pyridyl ureas) and 4,331,807 (N-(4-pyridazinyl)-N'-phenylureas).

SUMMARY OF THE INVENTION

A new class of plant regulating compounds has now been found. The compounds are pyridazinylureas of the formula (I):

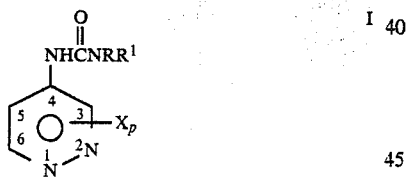

and acid addition salts thereof; wherein R is alkyl or cycloalkyl; $R^1$ is hydrogen or alkyl; each X independently is halogen, alkoxy, alkylthio or alkylsulfonyl; and p is 0, 1 or 2.

The compounds exhibit plant regulatory activity in terms of one or more of stunting, dessication, axillary growth stimulation, nastic response, growth stimulation, defoliation, intumescence, negative root geotropism, darker green basal leaves, leaf alteration and retardation of senescence.

DETAILED DESCRIPTION

In formula I, R, $R^1$ and X may contain any number of carbon atoms and any form of branching, for example, 1 to 20 carbon atoms or more. However, 1 to 8 carbon atoms are preferred, more preferably 1 to 4 carbon atoms in the case of all groups other than cycloalkyl, from the standpoint of ease of synthesis. The cycloalkyl group preferably will contain 3 to about 10 carbon atoms, such as cyclopentyl, cyclohexyl and cycloheptyl. "Halogen" means chloro, bromo, fluoro and iodo, preferably in that order, and includes mixed halogens when p is 2.

When X in formula I is halogen, such as chloro, plant regulator activity of the compounds is greater if the halogen is in the 5- and/or 6-position on the pyridazinyl ring.

The acid addition salts of the compounds of formula I include organic and inorganic salts such as the hydrochlorides, sulfates, phosphates, citrates and tartrates.

The compounds of formula I wherein R is other than cycloalkyl are prepared in a generally known manner by nitrating pyridazine with a mixture of fuming sulfuric and nitric acids, reducing the nitro group to amino by hydrogenation over palladium on carbon, and coupling with an isocyanate (R—NCO). For preparation of compounds of formula I wherein R is alkyl or cycloalkyl and R' is alkyl, the amino intermediate is reacted with phenyl chloroformate to form a phenyl N-(pyridazinyl)carbamate intermediate which is then reacted with an alkyl amine (mono or di) or a cycloalkyl amine to form the corresponding monoalkyl, dialkyl or cycloalkyl product. Alternatively, an aminopyridazine intermediate is prepared by aminating a chloropyridazine and hydrogenating over palladium on carbon. The aminopyridazine is then reacted with an appropriate isocyanate (R—NCO) to form the pyridazinyl urea. The reactions are conducted in appropriate organic solvents with appropriate pressure and temperature controls. The work-up and isolation procedures are conventional.

Further details of synthesis are given in the representative examples below. Table I following the examples lists the compounds of the examples and other compounds of the invention. In compound 6 of Table I, p is 2. In all other compounds of Table I, p is 1 or 0 (X=hydrogen).

EXAMPLE 1

Synthesis of N-(4-pyridazinyl)-N'-(1-methylethyl) urea (Compound No. 1)

Step A: 4-Aminopyridazine

A solution of 10.1 grams (0.055 mole) of 3,4,5-trichloropyridazine in 100 ml of absolute ethanol, in a 200 ml pressure bottle, is cooled to 0° C. and saturated with ammonia gas. The bottle is sealed and the reaction mixture stirred at ambient temperature for 4 days. The reaction mixture is purged with nitrogen for 2 hours, then filtered to remove ammonium chloride. The filter cake is washed with anhydrous ethanol. The filtrate and washes are placed in a Parr hydrogenation bottle and 5.2 grams (0.13 mole) of sodium hydroxide and 0.6 gram of 10% palladium on carbon are added. The volume of the mixture is brought to 200 ml with absolute ethanol. The mixture is hydrogenated for 4 hours using a Parr hydrogenator, during which time the theoretical amount of hydrogen is taken up. The hydrogenation bottle is purged with nitrogen and the reaction mixture filtered through diatomaceous earth. The filtrate is concentrated under reduced pressure to a residue. The residue is dried under reduced pressure at ambient temperature for several hours. The residue is triturated with 250 ml of ethyl acetate, and the mixture allowed to stand for 7 days under anhydrous conditions. The mixture is filtered to collect a solid, which is dried under reduced pressure at 40° C. to yield 3.9 grams of 4-aminopyridazine. The nmr spectrum is consistent with the proposed structure.

Step B: N-(4-pyridazinyl)-N'-(1-methylethyl)urea

To a stirred solution of 2.3 grams (0.024 mole) of 4-aminopyridazine (prepared as in Example 1, Step A) and 0.5 gram (0.004 mole) of 1,4-diazabicyclo[2.2.2]octane in 20 ml of dimethylformamide is added dropwise 3.3 ml (0.033 mole) of (1-methylethyl) isocyanate. Upon completion of addition the reaction mixture is stirred at ambient temperature for two days. The reaction mixture is concentrated under reduced pressure and the solid residue dried at 60°–70° C. The solid is stirred with ethanol and collected by filtration to yield 1.9 grams of N-(4-pyridazinyl)-N'-(1-methylethyl)urea; m.p. 206°–209° C. then 266°–269° C. The nmr spectrum is cnsistent with the proposed structure.

EXAMPLE 2

Synthesis of N-(4-pyridazinyl)-N'-cyclopentylurea
(Compound No. 9)

Step A: Phenyl N-(4-pyridazinyl)carbamate

A stirred suspension of 2.6 grams (0.027 mole) of 4-aminopyridazine (prepared as in Example 1, Step A) in 100 ml of tetrahydrofuran is cooled to 0° C. and 4.6 ml (0.033 mole) of triethylamine is added in one portion. A solution of 4.1 ml (0.033 mole) of phenyl chloroformate in tetrahydrofuran is added dropwise during a 30 minute period. Upon completion of addition the reaction mixture is allowed to warm to ambient temperature where it is stirred for three days. The reaction mixture is concentrated under reduced pressure to a residue. The residue is taken up in 500 ml of chloroform and filtered to collect 1.9 grams of phenyl N-(4-pyridazinyl)carbamate; m.p. 184°–185° C. The filtrate is washed with water, then dried with magnesium sulfate. The mixture is filtered and the filtrate placed on a column of silica gel. Further elution is accomplished using 10% methanol in methylene chloride. The appropriate fractions are combined and concentrated under reduced pressure to yield an additional 1.8 grams of phenyl N-(4-pyridazinyl)carbamate. The nmr spectra are consistent with the proposed structure. The reaction is repeated several times.

Step B: N-(4-pyridazinyl)-N'-cyclopentylurea

A stirred solution of 2.0 grams (0.009 mole) of phenyl N-(4-pyridazinyl)carbamate and 1.0 ml (0.010 mole) of cyclopentylamine in tetrahydrofuran is heated under reflux for 18 hours. The reaction mixture is filtered and the filtrate concentrated under reduced pressure to a residue. The residue is purified by column chromatography on silica gel. Elution is accomplished with 10% methanol in methylene chloride. The appropriate fractions are combined and concentrated under reduced pressure to yield 0.2 gram of N-(4-pyridazinyl)-N'-cyclopentylurea. This material is combined with the identical product from a previous reaction to yield 0.5 gram; m.p. 192°–195° C., dec. The nmr spectrum is consistent with the proposed structure. The reaction is repeated several times.

EXAMPLE 3

Synthesis of N-(4-pyridazinyl)-N'-cycloheptylurea
(Compound No. 11)

This compound is prepared in the manner of Example 2, Step B, using 4.0 grams (0.019 mole) of phenyl N-(4-pyridazinyl)carbamate and 2.1 grams (0.019 mole) of cycloheptylamine in tetrahydrofuran. The yield of N-(4-pyridazinyl)-N'-cycloheptylurea is 2.0 grams; m.p. 226°–228° C. The nmr spectrum is consistent with the proposed structure. The reaction is repeated several times.

EXAMPLE 4

Synthesis of N-(6-chloro-4-pyridazinyl)-N'-(1-methylethyl)urea
(Compound No. 2)

Step A: 3-hydrazino-4-amino-6-chloropyridazine

A stirred solution of 2.0 grams of 4-amino-3,6-dichloropyridazine and 2.5 ml of hydrazine hydrate in 20 ml of ethanol is heated under reflux for three hours. After this time water is added to the reaction mixture and the resultant precipitate collected by filtration. The filter cake is recrystallized from ethanol to yield 2.3 grams of 3-hydrazino-4-amino-6-chloropyridazine; m.p. 190° C.

Step B: 4-amino-6-chloropyridazine

A stirred solution of 1.2 grams of 3-hydrazino-4-amino-6-chloropyridazine and 15 ml of aqueous 8% sodium hydroxide solution is heated under reflux for 30 minutes. The reaction mixture is treated with decolorizing carbon and filtered. The filtrate is neutralized with aqueous 50% acetic acid and the resultant precipitate is collected by filtration. The filter cake is recrystallized from water to yield 0.8 gram of 4-amino-6-chloropyridazine, m.p. 153°–154.5° C.

Step C: N-(6-Chloro-4-pyridazinyl)-N'-(1-methylethyl)urea

To a stirred solution of 0.8 gram of 4-amino-6-chloropyridazine in 30 ml of dimethylformamide is added 0.2 gram of 1,4-diazabicyclo[2.2.2]octane, followed by 0.6 gram of 1-methylethyl isocyanate. The reaction mixture is stirred at ambient temperature for 18 hours, then at 60° C. for six hours. The majority of the dimethylformamide is removed under reduced pressure, and the residue is slurried in water. The resultant solid is collected by filtration and dried to yield N-(6-chloro-4-pyridazinyl)-N'-(1-methylethyl)urea.

EXAMPLE 5

Synthesis of N-(5,6-dichloro-4-pyridazinyl)-N'-(1-methylethyl)urea
(Compound No. 6)

Step A: 4,5-dichloro-3-pyridazone

A stirred solution of 3.9 grams of mucochloric acid in water is warmed to 8°–100° C., and a mixture of 3.1 grams of hydrazine sulfate and 3.0 grams of sodium acetate is added. A solid is collected by filtration and recrystallized from water to yield 3.0 grams of 4,5-dichloro-3-pyridazone; m.p. 199°–200° C. The reaction is repeated several times.

Step B: 3,4,5-trichloropyridazine

A stirred solution of 20.0 grams of 4,5-dichloro-3-pyridazone in 150 ml of phosphorus oxychloride is heated under reflux for five hours. The excess phosphorus oxychloride is removed under reduced pressure, and the residue poured into ice water. The mixture is extracted with diethyl ether. The extract is dried with magnesium sulfate, filtered, and the filtrate concentrated to a residue. The residue is distilled under reduced pressure. A fraction, b.p. 117°–118° C./14–15 mm, 20 grams, solidifies on standing. The solid is recrystallized from acetone-water to yield 3,4,5-trichloropyridazine; m.p. 61° C.

Step C: Mixture of aminodichloropyridazines

Dry ethanol is saturated with ammonia gas and placed in a sealed tube with 8.0 grams of 3,4,5-trichloropyridazine. The reaction mixture is heated at 120°–130° C. for five hours. The tube is opened and the reaction mixture concentrated under reduced pressure. The residue is dissolved in 20 ml of chloroform and the solution heated under reflux for 20 minutes. The solution is allowed to cool to ambient temperature for several hours in place. A solid precipitate is collected by filtration and repeatedly recrystallized from water to yield 2.8 grams of 4-amino-3,5-dichloropyridazine; m.p. 176°–178° C. The filtrate is concentrated under reduced pressure and the residue recrystallized from water to yield 2.0 grams of 4-amino-5,6-dichloropyridazine; m.p. 150°–151° C.

Step D: Phenyl N-(5,6-dichloro-4-pyridazinyl)carbamate

A stirred suspension of 2.0 grams (0.012 mole) of 4-amino-5,6-dichloropyridazine in 75 ml of tetrahydrofuran is cooled to 0° C. and 1.5 grams (0.015 mole) of triethylamine is added in one portion. A solution of 2.3 grams (0.015 mole) of phenyl chloroformate in tetrahydrofuran is added dropwise during a 30 minute period. Upon completion of addition the reaction mixture is allowed to warm to ambient temperature where it is stirred for three days. The reaction mixture is taken up in 500 ml of chloroform and filtered to collect 0.98 gram of phenyl N-(5,6-dichloro-4-pyridazinyl)carbamate. The filtrate is concentrated under reduced pressure to a residue. The residue is subjected to column chromatography on silica gel to yield an additional 0.9 gram of phenyl N-(5,6-dichloro-4-pyridazinyl)carbamate.

Step E: N-(5,6-dichloro-4-pyridazinyl)-N'-(1-methylethyl)urea

A stirred solution of 1.0 gram (0.004 mole) of phenyl N-(5,6-dichloro-4-pyridazinyl)carbamate and 0.27 gram (0.005 mole) of 1-methylethylamine in tetrahydrofuran is heated under reflux for 18 hours. The reaction mixture is filtered and the filtrate concentrated under reduced pressure to a residue. The residue is purified by column chromatography to yield 0.1 gram of N-(5,6-dichloro-4-pyridazinyl)-N'-(1-methylethyl)urea.

EXAMPLE 6

Synthesis of N-(4-pyridazinyl)-N'-cyclopentyl-N'-methylurea (Compound No. 12)

A stirred solution of 2.0 grams of phenyl N-(4-pyridazinyl)carbamate (prepared as in Example 2, Step A) and 0.9 gram of N-cyclopentyl-N-methyl amine in tetrahydrofuran is heated under reflux for 18 hours. The reaction mixture is filtered and the filtrate concentrated under reduced pressure to a residue. The residue is purified by column chromatography on silica gel to yield N-(4-pyridazinyl)-N'-cyclopentyl-N'-methylurea.

TABLE I

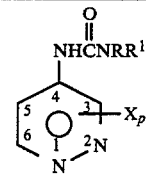

| Cmpd. No. | R | $R^1$ | X | Name |
|---|---|---|---|---|
| 1 | $-CHCH_3(CH_3)$ | H | — | N—(4-pyradazinyl)-N'—(1-methylethyl)urea |
| 2 | $-CHCH_3(CH_3)$ | H | 6-chloro | N—(6-chloro-4-pyridazinyl)-N'—(1-methylethyl)urea |
| 3 | $-CHCH_3(CH_3)$ | H | 6-OCH$_3$ | N—(6-methoxy-4-pyridazinyl)-N'—(1-methylethyl)urea |
| 4 | $-CHCH_3(CH_3)$ | H | 6-SCH$_3$ | N—(6-methylthio-4-pyridazinyl)-N'—(1-methylethyl)urea |
| 5 | $-CHCH_3(CH_3)$ | H | 6-SO$_2$CH$_3$ | N—(6-methylsulfonyl-4-pyridazinyl)-N'—(1-methylethyl)urea |
| 6 | $-CHCH_3(CH_3)$ | H | 5,6-dichloro | N—(5,6-dichloro-4-pyridazinyl)-N'—(1-methylethyl)urea |
| 7 | $-C_4H_9$ | $-CH_3$ | — | N—(4-pyridazinyl)-N'—butyl-N'—methylurea |
| 8 | $-C(CH_3)_3$ | $-CH_3$ | — | N—(4-pyridazinyl)-N'—(1,1-dimethylethyl)-N'—methylurea |
| 9 | $-C_5H_9$ | H | — | N—(4-pyridazinyl)-N'—cyclopentylurea |
| 10 | $-C_6H_{11}$ | H | — | N—(4-pyridazinyl)-N'—cyclohexylurea |
| 11 | $-C_7H_{13}$ | H | — | N—(4-pyridazinyl)-N'—cycloheptylurea |
| 12 | $-C_5H_9$ | $CH_3$ | — | N—(4-pyridazinyl)-N'—cyclopentyl-N'—methylurea |

TABLE I-continued

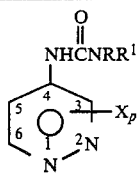

| Cmpd. No. | R | R¹ | X | Name |
|---|---|---|---|---|
| 13 | —C$_6$H$_{11}$ | CH$_3$ | — | N—(4-pyridazinyl)-N'—cyclohexyl-N'—methylurea |
| 14 | —C$_2$H$_5$ | H | — | N—(4-pyridazinyl)-N'—ethylurea |
| 15 | —C$_4$H$_9$ | H | — | N—(4-pyridazinyl)-N'—butylurea |
| 16 | —C(CH$_3$)$_3$ | H | — | N—(4-pyridazinyl)-N'—(1,1-dimethylethyl)urea |

PLANT REGULATOR UTILITY

The pyridazinylurea compounds of the invention exhibit various forms of plant regulator activity when tested in vitro and in whole plant assays as described more particularly hereinbelow. Briefly, such activity is apparent in preemergence and postemergence plant response screens on a variety of plants, particularly soybean and cotton, where morphological responses include stunting, axillary growth stimulation, nastic response, defoliation, darker green basal leaves, and some herbicidal activity. In antisenescence assays, compounds of the invention cause retention of chlorophyll in excised wheat leaves and in soybean leaves and pods, while reducing abscission, thus indicating ability to retard senescence.

The plant regulators of this invention are effectively employed as plant regulators in a number of broadleafed and grain crops, for example, soybean, lima bean, wheat, rice, corn, sorghum, and cotton, and turf grasses.

The plant regulator compounds, like most agricultural chemicals, are generally not applied full strength, but are formulated with agriculturally acceptable carriers or extenders (diluents) normally employed for facilitating the dispersion of active ingredients and various additives, and optionally with other active ingredients, recognizing that the formulation and mode of application of the active component may affect the activity of the material. The present compounds may be applied, for example, as powders or liquids, the choice of application varying with the plant species and environmental factors present at the particular locus of application. Thus, the compounds may be formulated as emulsifiable concentrates, wettable powders, flowable formulations, solutions, dispersions, suspensions and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, by suitably present at a concentration of from about 0.5% up to about 99.5% by weight of the formulation. Substantially inactive ingredients such as adjuvants, diluents, and carriers may comprise from about 99.5% by weight to as low as about 0.5% by weight of the formulation. Surface active agents, if employed in the formulation, may be present at various concentrations, suitably in the range of 1 to 30% by weight. Provided below is a general description of representative formulations which may be employed for dispersion of the plant regulators of the present invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

The following are specific examples of emulsifiable concentrate formulations suitable for use in the present invention:

|  | % by Wt. |
|---|---|
| Formulation 1: |  |
| Active ingredient | 53.01 |
| Blend of alkylbenzenesulfonate salt and polyoxyethylene ethers | 6.00 |
| Epoxidized soybean oil | 1.00 |
| Xylene | 39.99 |
| Total | 100.00 |
| Formulation 2: |  |
| Active ingredient | 10.00 |
| Blend of alkylbenzenesulfonate salt and polyoxyethylene ethers | 4.00 |
| Xylene | 86.00 |
| Total | 100.00 |

Wettable powders, also useful formulations for plant regulators, are in the form of finely divided particles which disperse readily in water or other liquid vehicles. The wettable powder is ultimately applied to the plant as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency characteristics of the carrier. Liquids and low melting solids (m.p. 100° C.) are suitably formulated in the concentration range of 5 to 50% by weight, usually from 10 to 30%; high melting solids (mp 100° C.) being formulated in the range of 5 to 95% by weight, usually 50 to 85%. An agriculturally acceptable carrier or diluent, frequently including a small amount of a surfactant to facilitate wetting, dispersion and suspension, accounts for the balance of the formulation.

The following are specific examples for wettable powder formulations suitable for use in the present invention:

|  | % by Wt. |
|---|---|
| Formulation 3: | |
| Active ingredient | 40.00 |
| Sodium ligninsulfonate/sodium alkylnaphthalenesulfonate | 4.00 |
| Attapulgite clay | 56.00 |
| Total | 100.00 |
| Formulation 4: | |
| Active ingredient | 90.00 |
| Dioctyl sodium sulfosuccinate | 0.10 |
| Synthetic fine silica | 9.90 |
| Total | 100.00 |
| Formulation 5: | |
| Active ingredient | 20.00 |
| Sodium alkylnaphthalenesulfonate | 1.00 |
| Sodium ligninsulfonate | 4.00 |
| Attapulgite clay | 75.00 |
| Total | 100.00 |
| Formulation 6: | |
| Active ingredient | 25.00 |
| Base: | |
| 96% hydrated aluminum magnesium silicate | 75.00 |
| 2% powdered sodium ligninsulfonate | |
| 2% powdered anionic sodium alkylnaphthalenesulfonate | |
| Total | 100.00 |

Flowable formulations are similar to EC's except that the active ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

The following are specific examples of flowable formulations suitable for use in the present invention:

|  | % by Wt. |
|---|---|
| Formulation 7: | |
| Active Ingredient | 46.00 |
| Colloidal magnesium aluminum silicate | 0.40 |
| Sodium alkylnaphthalenesulfonate | 2.00 |
| Paraformaldehyde | 0.10 |
| Water | 41.42 |
| Propylene glycol | 7.50 |
| Acetylinic alcohols | 2.50 |
| Xanthan gum | 0.08 |
| Total | 100.00 |
| Formulation 8: | |
| Active ingredient | 45.00 |
| Water | 48.50 |
| Purified smectite clay | 2.00 |
| Xanthan gum | 0.50 |
| Sodium alkylnaphthalenesulfonate | 1.00 |
| Acetylinic alcohols | 3.00 |
| Total | 100.00 |

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include simple solutions or suspensions of the active ingredient in a relatively non-volatile solvent such as water, corn oil, kerosene, propylene glycol, or other suitable solvents. This type of formulation is particularly useful for ultra low volume application.

The following illustrate specific suspensions which are suitable for use in the present invention:

|  | % by Wt. |
|---|---|
| Formulation 9: | |
| Oil Suspension: | |
| Active ingredient | 25.00 |
| Polyoxyethylene sorbitol hexaoleate | 5.00 |
| Highly aliphatic hydrocarbon oil | 70.00 |
| Total | 100.00 |
| Formulation 10: | |
| Aqueous Suspension: | |
| Active ingredient | 40.00 |
| Polyacrylic acid thickener | 0.30 |
| Dodecylphenol polyethylene glycol ether | 0.50 |
| Disodium phosphate | 1.00 |
| Monosodium phosphate | 0.50 |
| Polyvinyl alcohol | 1.00 |
| Water | 56.70 |
| Total | 100.00 |

The concentration of the compound in use dilution is normally in the range of about 2% to about 0.1%. Many variations of spraying and dusting compositions in the art may be used by substituting or adding a compound of this invention into compositions known or apparent to the art.

The compositions may be formulated and applied with other suitable active ingredients, including nematicides, insecticides, acaricides, fungicides, other plant regulators, herbicides, fertilizers, etc.

In applying the foregoing chemicals, an effective growth regulating amount of the active ingredient must be applied. While the application rate will vary widely depending on the choice of compound, the formulation and mode of application, the plant species being treated and the planting density, a suitable use rate may be in the range of 0.1 to 10 kg/hectare, preferably 0.05 to about 5 kg/hectare.

The compounds of the invention were tested for plant regulator activity, first in a whole plant response screen and then in excised wheat leaf and soybean whole plant antisenescence tests.

PLANT RESPONSE SCREEN

In this assay the test compounds are applied as water-acetone (1:1) solutions, containing 0.5% v/v sorbitan monolaurate solubilizer, at a rate equivalent to 8.0 kg/ha, preemergently to planted seeds of test plants and postemergently to foliage of test plants. The test plants are soybean, cotton, corn, wheat, field bindweed, morningglory, velvetleaf, barnyardgrass, green foxtail and johnsongrass.

Compound Nos. 1, 9, 10, 11, 14 and 15 when thus-tested exhibited various forms and degrees of plant regulator activity, although not against all of the plants and to the same degree in each case. Generally, the test compounds were more active when applied post-emergently. Compound Nos. 9 and 15 were the most responsive of the test compounds, exhibiting 50 to 70% growth control against the cotton and soybean post-emergence test plants and varying forms and degrees of other regulator activity against the same and other plants, including stunting, auxiliary growth stimulation, defoliation, intumescence and darker green basal leaves. Some herbicidal activity was exhibited at the exceptionally high application rate of the tests.

WHEAT LEAF ANTISENESCENCE

In this test leaves were excised from wheat seedlings (*Triticum aestivum* cv. Prodax), weighed and placed in vials containing solutions of test compound in water-acetone (1:1) at concentrations of 25 ppm and 2.5 ppm. Wheat leaves were similarly placed in vials containing only deionized water, as controls. After four days of incubation at 30° C. in the dark, the test vilas were examined visually and given a numeric rating of 0 (color similar to color of the leaves in the control vials) or 1 (more green than the leaves in the control vials). The control leaves had yellowed, indicating loss of chlorophyll. The test results are set forth in Table II below, from which it will be noted that treatment at 25 ppm caused chlorophyll retention, whereby retarding senescence.

TABLE 11

| Cmpd No. | Chlorophyll Retention Concentration (ppm) | Visual Rating |
|---|---|---|
| 1 | 25 | 1 |
| | 2.5 | 0 |
| 9 | 25 | 1 |
| | 2.5 | 0 |
| 10 | 25 | 1 |
| | 2.5 | 0 |
| 11 | 25 | 1 |
| | 2.5 | 0 |
| 14 | 25 | 1 |
| | 2.5 | 0 |
| 15 | 25 | 1 |
| | 2.5 | 0 |

I claim:

1. A method of retarding senescence in soybean and cotton plants which comprises applying to the plant a plant regulating amount of a pyridazinylurea compound of the formula:

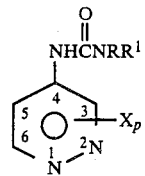

and acid addition salts thereof; wherein R is alkyl($C_1$–$C_8$) or cycloalkyl($C_3$–$C_{10}$), $R^1$ is hydrogen or alkyl($C_1$–$C_8$), each X independently is halogen, alkoxy($C_1$–$C_8$), alkyl($C_1$–$C_8$)thio or alkyl($C_1$–$C_8$)sulfonyl, and p is 0, 1 or 2.

2. The method of claim 1 wherein the compound is selected from
N-(4-pyridazinyl)-N'-cyclopentylurea,
N-(4-pyridazinyl)-N'-cyclopentyl-N'-methylurea,
N-(4-pyridazinyl)-N'-cycloheptylurea,
N-(4-pyridazinyl)-N'-cyclohexylurea,
N-(4-pyridazinyl)-N'-(1-methylethyl)urea,
N-(4-pyridazinyl)-N'-(1,1-dimethylethyl)urea,
N-(4-pyridazinyl)-N'-ethylurea,
N-(4-pyridazinyl)-N'-n-butyl-N'-methylurea,
N-(6-chloro-4-pyridazinyl)-N'-(1-methylethyl)urea and
N-(5,6-dichloro-4-pyridazinyl)-N'-(1-methylethyl)urea.

3. The method of claim 1 wherein the pyridazinylurea compound is N-(4-pyridazinyl)-N'-cyclopentylurea.

4. The method of claim 1 wherein the pyridazinylurea compound is N-(4-pyridazinyl)-N'-cycloheptylurea.

5. The method of claim 1 wherein the pyridazinylurea compound is N-(4-pyridazinyl)-N'-cyclohexylurea.

6. The method of claim 1 wherein the pyridazinylurea compound is N-(4-pyridazinyl)-N'-(1-methylethyl)urea.

7. The method of claim 1 wherein the pyridazinylurea compound is N-(4-pyridazinyl)-N'-(1,1-dimethylethyl)urea.

8. The method of claim 1 wherein the pyridazinylurea compound is N-(4-pyridazinyl)-N'-ethylurea.

* * * * *